United States Patent
Edwards et al.

(10) Patent No.: US 6,740,310 B2
(45) Date of Patent: May 25, 2004

(54) POROUS PARTICLES COMPRISING EXCIPIENTS FOR DEEP LUNG DELIVERY

(75) Inventors: David A. Edwards, Boston, MA (US); Giovanni Caponetti, Somerville, MA (US); Jeffrey S. Hrkach, Cambridge, MA (US); Noah Lotan, Haifa (IL); Justin Hanes, Baltimore, MD (US); Robert S. Langer, Newton, MA (US); Abdellaziz Ben-Jebria, State College, PA (US)

(73) Assignees: Massachusetts Institute of Technology, Cambridge, MA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 10/209,654

(22) Filed: Jul. 30, 2002

(65) Prior Publication Data

US 2003/0012742 A1 Jan. 16, 2003

Related U.S. Application Data

(63) Continuation of application No. 09/888,688, filed on Jun. 25, 2001, now Pat. No. 6,436,443, which is a continuation of application No. 09/569,153, filed on May 11, 2000, now Pat. No. 6,254,854, which is a continuation of application No. 08/655,570, filed on May 24, 1996, now abandoned.

(51) Int. Cl.$^7$ .............................. A61K 9/12; A61K 9/14
(52) U.S. Cl. ...................... 424/45; 424/46; 424/489; 424/491; 424/499; 514/2; 514/3
(58) Field of Search ............................ 424/45, 46, 489, 424/491, 499, 130.1; 514/2, 3; 128/203.15

(56) References Cited

U.S. PATENT DOCUMENTS

| | | |
|---|---|---|
| 4,161,516 A | 7/1979 | Bell |
| 4,272,398 A | 6/1981 | Jaffe |
| 4,590,206 A | 5/1986 | Forrester et al. |
| 4,741,872 A | 5/1988 | De Luca et al. |
| 4,818,542 A | 4/1989 | De Luca et al. |
| 4,855,144 A | 8/1989 | Leong et al. |
| 4,857,311 A | 8/1989 | Domb et al. |
| 4,865,789 A | 9/1989 | Castro et al. |
| 4,904,479 A | 2/1990 | Illum |
| 5,069,936 A | 12/1991 | Yen |
| 5,145,684 A | 9/1992 | Liversidge et al. |
| 5,160,745 A | 11/1992 | De Luca et al. |
| 5,169,871 A | 12/1992 | Hughes et al. |
| 5,260,306 A | 11/1993 | Boardman et al. |
| 5,384,133 A | 1/1995 | Boyes et al. |
| 5,456,917 A | 10/1995 | Wise et al. |
| 5,458,135 A | 10/1995 | Patton et al. |
| 5,506,203 A | 4/1996 | Bäckström et al. |
| 5,518,998 A | 5/1996 | Bäckström et al. |
| 5,607,695 A | 3/1997 | Ek et al. |
| 5,612,053 A | 3/1997 | Baichwal et al. |
| 5,642,728 A | 7/1997 | Andersson et al. |
| 5,690,954 A | 11/1997 | Illum |
| 5,707,644 A | 1/1998 | Illum |
| 5,780,014 A | 7/1998 | Eljamal et al. |
| 5,795,594 A | 8/1998 | York et al. |
| 5,804,212 A | 9/1998 | Illum |
| 5,830,853 A | 11/1998 | Bäckström et al. |
| 5,851,453 A | 12/1998 | Hanna et al. |
| 5,855,913 A | 1/1999 | Hanes et al. |
| 5,874,064 A | 2/1999 | Edwards et al. |
| 5,985,309 A | 11/1999 | Edwards et al. |
| 5,997,848 A | 12/1999 | Patton et al. |
| 6,063,138 A | 5/2000 | Hanna et al. |
| 6,165,463 A * | 12/2000 | Platz et al. ............... 424/130.1 |
| 6,254,854 B1 * | 7/2001 | Edwards et al. ............... 424/46 |
| 6,423,344 B1 | 7/2002 | Platz et al. |
| 6,436,443 B2 * | 8/2002 | Edwards et al. ............ 424/489 |

FOREIGN PATENT DOCUMENTS

| | | |
|---|---|---|
| EP | 0 072 046 | 2/1983 |
| EP | 0 257 915 | 3/1988 |
| EP | 0 335 133 | 10/1989 |
| WO | WO 91/04732 | 4/1991 |
| WO | WO 94/07514 | 4/1994 |
| WO | WO 95/00127 | 1/1995 |
| WO | WO 95/07072 | 3/1995 |
| WO | WO 95/24183 | 9/1995 |
| WO | WO 96/09814 | 4/1996 |
| WO | WO 97/36574 | 10/1997 |
| WO | WO 99/16419 | 4/1999 |
| WO | WO 99/16420 | 4/1999 |
| WO | WO 99/16421 | 4/1999 |
| WO | WO 99/16422 | 4/1999 |

OTHER PUBLICATIONS

Clay, M.M., et al. "Effect of Aerosol Particle Size on Bronchodilatation with Nebulised Terbutaline in Asthmatic Subjects," *Thorax* 41:364–368(1986).

(List continued on next page.)

Primary Examiner—Michael G. Hartley
Assistant Examiner—Mina Haghighatian
(74) Attorney, Agent, or Firm—Elmore Craig, P.C.; Carolyn S. Elmore; Anne I. Craig

(57) ABSTRACT

Improved porous particles for drug delivery to the pulmonary system, and methods for their synthesis and administration are provided. In a preferred embodiment, the porous particles are made of a biodegradable material and have a mass density less than 0.4 g/cm$^3$/. The particles may be formed of biodegradable materials such as biodegradable polymers. For example, the particles may be formed of a functionalized polyester graft copolymer consisting of a linear a-hydroxy-acid polyester backbone having at least one amino acid group incorporated therein and at least one poly(amino acid) side chain extending from an amino acid group in the polyester backbone. In one embodiment, porous particles having a relatively large mean diameter, for example greater than 5 μm, can be used for enhanced delivery of a therapeutic agent to the alveolar region of the lung. The porous particles incorporating a therapeutic agent may be effectively aerosolized for administration to the respiratory tract to permit systemic or local delivery of wide variety of therapeutic agents.

23 Claims, 2 Drawing Sheets

OTHER PUBLICATIONS

Cohen, S., et al., "Controlled Delivery Systems for Proteins Based on Poly(Lactic/Glycolic Acid) Microspheres," *Pharm. Res.* 8(6):713–720(1991).

Daly, W.H., et al., "The Preparation of N–Carboxyanhydrides of α–Amino Acids Using Bis(Trichloromethyl) Carbonate," *Tetrahedron Lett.*, 29(46):5859–5862 (1988).

Damms, B. and W. Bains, "The Cost of Delivering Drugs without Needles," *J. Controlled Release*, 8–11 (1996).

Davies, C.N., et al., "Breathing of Half–micron Aerosols. I. Experimental.," *J. of Appl. Physiol.* 32(5):591–600(1972).

Dorries, A.M., and Valberg P.A., "Heterogeneity of Phagocytosis for Inhaled Versus Instilled Material," *Am. Rev. Respir. Dis.*, 146:831–837 (1992).

Kricheldorf, H.R. "α–Aminoacid–N–Carboxy–Anhydrides and Related Heterocycles," Springer–Verlag, Berlin (1987).

Edwards, D.A., "The Macrotransport of Aerosol Particles in the Lung: Aerosol Deposition Phenomena," *J. Aerosol Sci.*, 26(2):293–317 (1995).

Eldridge, J. H., et al., "Biodegradable Microspheres as a Vaccine Delivery System," *Mol. Immunol.*, 28(3):287–294 (1991).

Findeisen, W. "Uber Das Absetzen Kleiner, in Der Luft Suspendierter Teilchen in Der Menshlichen Lunge Bei Der Atmung," *Pflugers Arch. D. Ges. Physiol.* 236:367–379 (1935).

French, D.L, et al., "The Influence of Formulation on Emission, Deaggregation and Deposition of Dry Powders for Inhalation," *J. Aerosol Sci.*, 27(5):769–783 (1996).

Ganderton, D., "The Generation of Respirable Clouds Form Coarse Powder Aggregates," *J. Biopharmaceutical Sciences*, 3(1/2):101–105 (1992).

Gehr, P. et al., "Surfactant and Inhaled Particles in the Conducting Airways: Structural, Stereological, and Biophysical Aspects," *Microscopy Res. And Tech.*, 26:423–436 (1993).

Gerrity, T.R., et al., "Calculated Deposition of Inhaled Particles in the Airway Generations of Normal Subjects," *J. Appl. Phys.*, 47(4):867–873 (1979).

Morén, F., "Aerosol Dosage Forms and Formulations," in *Aerosols in Medicine. Principles, Diagnosis and Therapy*, Morén, et al., Eds, Elsevier, Amsterdam, 1985.

Morimoto, Y., and Adachi, Y., "Pulmonary Uptake of Liposomal Phosphatidylcholine Upon Intratracheal Administration to Rats," *Chem. Pharm. Bull.* 30(6):2248–2251 (1982).

Mulligan, R.C., "The Basic Science of Gene Therapy", *Science*, 260:926–932 (1993).

Mumenthaler, M., et al., "Feasibility Study on Spray–Drying Protein Pharmaceuticals: Recombinant human Growth Hormone and Tissue–Type Plasminogen Activator," *Pharm. Res.*, 11(1):12–20 (1994).

Niven, R.W., et al., "The Pulmonary Absorption of Aerosolized and Intratracheally Instilled rhG–CSF and monoP-EGylated rhG–CSF," *Pharm. Res.*, 12(9):1343–1349 (1995).

Okumura, K., et al., "Intratracheal Delivery of Insulin. Absorption from Solution and Aerosol by Rat Lung," *Int. J. Pharmaceutics*, 88:63–73 (1992).

Patton, J.S., and R.M. Platz, "(D) Routes of Delivery: Case Studies (2) Pulmonary Delivery of Peptides and Proteins for Systemic Action", *Adv. Drug Del. Rev.*, 8:179–196 (1992).

Patton, J.S., et al., "Bioavailability of pulmonary delivered peptides and proteins: α–interferon, calcitonins and parathyriod hormones," *J. Controlled Release*, 28:79–85 (1994).

Pavia, D., "Lung Mucociliary Clearance". In *Aerosols and the Lung: Clinical and Experimental Aspects*, Clarke, S.W. and Pavia, D., eds. (Butterworths, London), pp. 127–155, (1984).

Landahl, "On The Removal of Air–borne Droplets by The Human Respiratory Tract: I. The Lung," *Bull. Math. Biophys.*, 12:43–56 (1950).

Timsina, M.P., et al., "Drug Delivery to the Respiratory Tract Using Dry Powder Inhalers," *Int. J. of Pharm.*, 101:1–13 (1994).

Adjei, A., and Garren, J., "Pulmonary Delivery of Peptide Drugs: Effect of Particle Size on Bioavailability of Leuprolide Acetate in Healthy Male Volunteers," *Pharm. Res.*, 7(6):565–569 (1990).

Altshuler, B., et al., "Aerosol Deposition in the Human Respiratory Tract," *Am. Med. Assoc. Arch. of Indust. Health* 15:293–303 (1957).

Anderson, P.J., et al., "Effect of Cystic Fibrosis on Inhaled Aerosol Boluses," *Am. Rev. Respir. Dis.*, 140:1317–1324 (1989).

Pinkerton, K.E., et al., "Aerosolized Fluorescent Microspheres Detected in the Lung Using Confocal Scanning Laser Microscopy", *Microscopy Res. and Tech.*, 26:437–443 (1993).

Colthorpe, P., et al., "The Pharmacokinetics of Pulmonary-–Delivered Insulin: A Comparison of Intratracheal and Aerosol Administration to the Rabbit," *Pharm. Res.* 9(6):764–768 (1992).

Rudt, S., and R.H. Muller, "In Vitro Phagocytosis Assay of Nano–and Microparticles by Chemiluminescence. I. Effect of Analytical Parameters, Particle Size and Particle Concentration," *J. Contr. Rel.*, 22:263–271 (1992).

Rudt, S., et al., "In Vitro Phagocytosis Assay of Nano–and Microparticles by Chemiluminescence. IV. Effect of Surface Modification by Coating of Particles with Poloxamine and Antarox CO on the Phagocytic Uptake", *J. of Contr. Rel.* 25:123–132 (1993).

Ruffin, R.E., et al., "The Preferential Deposition of Inhaled Isoproterenol and Propranolol in Asthmatic Patients," *Chest* 80(6):904–907 (1981).

Sela, M., et al., "Multichain Polyamino Acids," *J. Am. Chem. Soc.*, 78:746–751 (1956).

Tabata, Y., et al., "Controlled Delivery Systems for Proteins Using Polyanhydride Microspheres," *Pharm. Res.* 10(4):487–496 (1993).

Swift, D., "The Oral Airway—A Conduit or Collector for Pharmaceutical Aerosols?" *Respiratory Drug Delivery IV*, 187–195 (1994).

Tabata, Y., and Y. Ikada, "Effect of Surface Wettability of Microspheres on Phagocytosis," *J. of Colloid and Interface Sci.*, 127(1):132–140 (1989).

Tabata, Y., and Y. Ikada, "Macrophage Phagocytosis of Biodegradable Microspheres Composed of L–lactic Acid/ glycolic Acid Homo–and Copolymers," *J. of Biomed. Mater. Res.*, 22:837–858 (1988).

Tabata, Y., and Ikada, Y., "Effect of Size and Surface Charge of Polymer Microspheres on Their Phagocytosis by Macrophage," *J. Biomed. Mater. Res.*, 22:837–843 (1988).

Barrera, D.A., et al., "Synthesis and RGD Peptide Modification of a New Biodegradable Copolymer: Poly(lactic acid–co–lysine)," *J. Am. Chem. Soc.*, 115:11010–11011 (1993).

Tansey, I.P., "The Challenges in the Development of Metered Dose Inhalation Aerosols Using Ozone–Friendly Propellants," *Spray Technol. & Market*, 4:26–29 (1994).

Turner, J.R., and S.V. Hering, "Greased and Oiled Substrates as Bounce–Free Impaction Surfaces," *J. Aerosol Sci.*, 18(2):215–224 (1987).

Lai, Y–L., et al., "Sustained Bronchodilation with Isoproterenol Poly(Glycolide–co–Lactide) Microspheres," *Pharm. Res.*, 10(1):119–125 (1993).

Visser, J., "An Invited Review: Van der Waals and Other Cohesive Forces Affecting Power Fludization," Power Technology, 58:1–10 (1989).

Wall, D.A., "Pulmonary Absorption of Peptides and Proteins," *Drug Delivery*, 2:1–20 (1995).

Warheit, D.B., and Hartsky, M.A., "Role of Alveolar Macrophage Chemotaxis and Phagocytosis in Pulmonary Clearance to Inhaled Particles: Comparisons Among Rodent Species," *Microscopy Res. and Tech.*, 26:412–422 (1993).

Langer, R., "New Methods of Drug Delivery", *Science*, 249:1527–1533 (1990).

Wong, M., and Suslick, K.S., "Sonochemically Produced Hemoglobin Microbubbles," *Mat. Res. Soc. Symp. Proc.*, 372:89–95 (1995).

Zanen, P., et al., "The Optimal Particle Size for β–adrenergic Aerosols in Mild Asthmatics", *Int. J. of Pharm.*, 107:211–217 (1994).

Zanen, P., et al., "The Optimal Particle Size for Parasympathicolytic Aerosols in Mild Asthmatics", *Int. J. of Pharm.*, 114:111–115 (1995).

Zeng, X.M., et al., "The Controlled Delivery of Drugs to the Lung," *Int. J. of Pharm.*, 124:149–164 (1995).

Edwards, D.A., et al., "Large Porous Particles for Pulmonary Drug Delivery," *Science* 276:1868–71 (1997).

Benita, S., et al., "Characterization of Drug–loaded Poly(d, l–lactide) Microspheres," *J. of Pharm. Sci* 73(12):1721–1724 (1984).

Wichert, B., and Rohdewald, P., "Low Molecular Weight PLA: A Suitable Polymer for Pulmonary Administered Microparticles?," *J. Microencapsulation*, 10(2):195–207 (1993).

Ménache, M.G., et al., "Particle Inhalability Curves for Humans and Small Laboratory Animals," *Annals of Occupational Hygiene*, 39(3):317–328 (1995).

Newman, S.P., "Aerosol Deposition Considerations in Inhalation Therapy," *Chest*, 88(2):152S–160S (1985).

Blackett, P.M., and G. Buckton, "A Microcalorimetric Investigation of the Interaction of Surfactants with Crystalline and Partially Crystalline Salbutamol Sulphate in a Model Inhalation Aerosol System," *Pharmaceutical Research*, 12(11):1689–1693 (1995).

Brain, J.D., "Physiology and Pathophysiology of Pulmonary Macrophages". In *The Reticuloendothelial System*, Reichard and Filkins, eds. (Plenum Press, New York), pp. 315–327 (1985).

Byron, P.R., "Determinants of Drug and Polypeptide Bioavailability from Aerosols Delivered to the Lung," *Adv. Drug. Del. Rev.*, 5:107–132 (1990).

Clark, A.R., and M. Egan, "Modeling the Deposition of Inhaled Powdered Drug Aerosols," *J. Aerosol Sci.*, 25(1):175–186 (1994).

Leone–Bay, A., et al., "Microsphere Formation in a Series of Derivatized α–Amino Acids: Properties, Molecular Modeling, and Oral Delivery of Salmon calcitonin," *J. of Med. Chem.*, 38(21):4257–4262 (1995).

Liu, F., et al., "Pulmonary Delivery of Free and Liposomal Insulin," *Pharm. Res.* 10(2):228–232 (1993).

Liu, W.R., et al., "Moisture–Induced Aggregation of Lyophilized Proteins in the Solid State," *Biotechnol. and Bioeng.*, 37:177–184 (1991).

Martonen, T.B., "Mathematical Model for the Selective Deposition of Inhaled Pharmaceuticals", *J. of Pharm. Sci.*, 82(12):1191–1198 (1993).

Masinde, L.E., and Hickey, A.J., "Aerosolized Aqueous Suspensions of Poly(L–Lactic Acid) Microspheres," *Int. J. of Pharmaceutics*, 100:123–131 (1993).

Mathiowitz, E., et al., "Novel Microcapsules for Delivery Systems," *Reactive Polymers*, 6:275–283 (1987).

Mathiowitz, E., et al., "Polyanhydride Microspheres. IV. Morphology and Characterization of Systems Made by Spray Drying," *J. of Appl. Polymer Sci.* 45:125–134 (1992).

Mathiowitz, E., et al., "Morphology of Polyanhydride Microsphere Delivery Systems," *Scanning Microscopy*, 4(2):329–340 (1990).

Mathiowitz, E., and R. Langer, "Polyanhydride Microspheres as Drug Carriers I. Hot–Melt Microencapsulation," *J. of Controlled Release* 5:13–22 (1987).

Mathiowitz, E., et al., "Polyanhydride Microspheres as Drug Carriers. II. Microencapsulation by Solvent Removal," *J. of Appl. Polymer Sci.*, 35:755–774 (1988).

Kwok, K.K., et al., "Production of 5–15 $\mu$m Diameter Alginate Polylysine Microcapsules by an Air Atomization Technique," Pharm. Res., 8(3):341–344 (1991).

Gonda, I., "Aerosols for Delivery of Therapeutic and Diagnostic Agents to the Respiratory Tract," in *Critical Reviews in Therapeutic Drug Carrier Systems*, 6:273–313 (1990).

Gonda, I., "Preface. Major Issues and Future Prospects in the Delivery of Therapeutic and Diagnostic Agents to the Respiratory Tract," *Adv. Drug Del. Rev.* 5:1–9 (1990).

Gonda, I., "Physico–chemical Principles in Aerosol Delivery," in *Topics in Pharmaceutical Sciences* 1991, Crommelin, D.J. and K.K. Midha, Eds., Medpharm Scientific Publishers, Stuttgart, pp. 95–117 (1992).

Gonda, I., "Targeting by Deposition," in Pharmaceutical Inhalation Aerosol Technology (ed. A.J. Hickey), Marcel Dekkar Inc., pp. 61–82, New York (1992).

Heyder, J., et al., "Deposition of Particles in the Human Respiratory Tract in the Size Range 0.005–15 $\mu$m," *J. Aerosol. Sci.*, 17(3):811–825 (1996).

Heyder, J., and G. Rudolf, "Mathematical models of particle deposition in the human respiratory tract," *J. Aerosol Sci.*, 15:697–707 (1984).

Heyder, J., et al., "Total Deposition of Aerosol Particles in the Human Respiratory Tract for Nose and Mouth Breathing," *J. Aerosol Sci.*, 6:311–328 (1975).

Hickey, A.J., et al., "Use of Particle Morphology to Influence the Delivery of Drugs from Dry Powder Aerosols," *J. Biopharmaceutical Sci.*, 3(½):107–113 (1992).

Hirano, S., et al., "Pulmonary Clearance and Toxicity of Zinc Oxide Instilled into the Rat Lung," *Arch. of Toxicology*, 63:336–342 (1989).

Hrkach, et al., "Synthesis of Poly(L–lactic acid–co–L–l-ysine) Graft Copolymers," *Macromolecules*, 28(13):4736–4739 (1995).

Hrkach, J.S., et al., "Poly(L–Lactic acid–co–amino acid) Graft Copolymers: A Class of Functional Biodegradable Biomaterials" in Hydrogels and Biodegradable Polymers for Bioapplications, ACS Symposium Series No. 627, Raphael M. Ottenbrite, et al., Eds., Americal Chemical Society, Chapter 8, pp. 93–101, 1996.

Johnson, M.A., et al. "Delivery of Albuterol and Ipratrophiumbromide from Two Nebulizer Systems in Chronic Stable Asthma: Efficacy and Pulmonary Deposition," *Chest*, 96:6–10 (1989).

Kassem, N.M., and D. Ganderton, "The Influence of Carrier Surface on the Characteristics of Inspirable Powder Aerosols," *J. Pharm. Pharmacol.*, 42(Supp):11 (1990).

Kawaguchi, H. et al., "Phagocytosis of Latex Particles by Leukocytes. I. Dependence of Phagocytosis on the Size and Surface Potential of Particles," *Biomaterials* 7:61–66 (1986).

Kobayashi, S. et al., "Pulmonary Delivery of Salmon Calcitonin Dry Powders Containing Absorption Enhancers in Rats," *Pharm. Res.*, 13(1):80–83 (1996).

Komanda, F. et al., "Intratracheal Delivery of Peptide and Protein Agents: Absorption from Solution and Dry Powder by Rat Lung," *J. Pharm. Sci.*, 83(6): 863–867 (June, 1994).

Krenis, L.J. and B. Strauss, "Effect of Size and Concentration of Latex Particles on Respiration of Human Blood Leucocytes," *Proc. Soc. Exp. Med.*, 107: 748–750 (1961).

Donbrow, Max., "Microcapsules & Nanoparticles in Medicine and Pharmacy," CRC Press, Boca Raton, 1992.

Illum, "Microspheres as a Potential Controlled Release Nasal Drug Delivery System" *Delivery Systems for Peptide Drugs*, NY: Plenum, 1986.

Kricheldorf, H.R. in "Models of Bipolymers by Ring–Opening Polymerization," Penczek, S., Ed. RC Press, Boca Raton, 1990, Chapter 1.

LeCorre, et al., "Preparation and Characterization of Bupivacaine–loaded Polylactide–co–glycolide Microspheres," Int J Pharmaceutics, 107:41–49 (1994).

Vincent, J. "Aerosol Science for Industrial Hygienists," Pergamon Press, NY (1995).

Weibel, W. "Morphometry of the Human Lung," Academic Press, NY (1963).

* cited by examiner

POROUS PARTICLES COMPRISING EXCIPIENTS FOR DEEP LUNG DELIVERY

RELATED APPLICATION(S)

This application is a Continuation of U.S. application Ser. No. 09/888,688 filed on Jun. 25, 2001, now U.S. Pat. No. 6,436,443 which is a Continuation of U.S. application Ser. No. 09/569,153 filed on May 11, 2000, now U.S. Pat. No. 6,254,854, which is a Continuation of U.S. application Ser. No. 08/655,570, filed May 24, 1996, now Abandoned; the entire teachings of all referenced applications and patents are incorporated herein by reference.

BACKGROUND OF THE INVENTION

The present invention relates generally to porous polymeric particles for drug delivery to the pulmonary system.

Biodegradable polymeric particles have been developed for the controlled-release and delivery of protein and peptides drugs. Langer, R., *Science,* 249: 1527–1533 (1990). Examples include the use of biodegradable particles for gene therapy (Mulligan, R. C. *Science,* 260: 926–932 (1993)) and "single-shot" vaccine delivery (Eldridge et al., *Mol. Immunol.,* 28: 287–294 (1991)) for immunization. Protein and peptide delivery via degradable particles is restricted due to low bioavailability in the blood stream, since macromolecules and/or microparticles tend to poorly permeate organ-blood barriers of the human body, particularly when delivered either orally or invasively.

Aerosols for the delivery of therapeutic agents to the respiratory tract have been developed. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems,* 6: 273–313, (1990). The deep lung, or alveoli, are the primary target of inhaled therapeutic aerosols for systemic delivery.

Inhaled aerosols have been used for the treatment of local lung disorders including asthma and cystic fibrosis (Anderson, et al., *Am. Rev. Rev. Respir. Dis.,* 140: 1317–1324 (1989)) and have potential for the systemic delivery of peptides and proteins as well (Patton and Platz, *Advanced Drug Delivery Reviews,* 8: 179–196 (1992)). However, pulmonary drug delivery strategies present many difficulties for the delivery of macromolecules; these include protein denaturation during aerosolization, excessive loss of inhaled drug in the oropharyngeal cavity (typically exceeding 80%), poor control over the site of deposition, irreproducibility of therapeutic results owing to variations in breathing patterns, the quick absorption of drug potentially resulting in local toxic effects, and phagocytosis by lung macrophages.

Local and systemic inhalation therapies can often benefit from a relative slow controlled release of the therapeutic agent. Gonda, I., "Physico-chemical principles in aerosol delivery," in: *Topics in Pharmaceutical Science* 1991, D. J. A. Crommelin and K. K. Midha, Eds., Stuttgart: Medpharm Scientific Publishers, pp. 95–117, 1992. Slow release from a therapeutic aerosol can prolong the residence of an administered drug in the airways or acini, and diminish the rate of drug appearance in the blood stream. Also, patient compliance is increased by reducing the frequency of dosing. Langer, R., *Science,* 249: 1527–1533 (1990); and Gonda, I., "Aerosols for delivery of therapeutic and diagnostic agents to the respiratory tract," in *Critical Reviews in Therapeutic Drug Carrier Systems,* 6: 273–313, 1990.

The human lungs can remove or rapidly degrade hydrolytically cleavable deposited aerosols over periods ranging from minutes to hours. In the upper airways, ciliated epithelia contribute to the "mucociliary excalator" by which particles are swept from the airways toward the mouth. Pavia, D., "LungMucociliary Clearance," in *Aerosols and the Lung: Clinical and Experimental Aspects*, Clarke, S. W. and Pavia, D., Eds., Butterworths, London, 1984. In the deep lungs, alveolar macrophages are capable of phagocytosing particles soon after their deposition. Warheit, M. B. and Hartsky, M. A., *Microscopy Res. Tech.,* 26: 412–422 (1993); and Brain, J. D., "Physiology and Pathophysiology of Pulmonary Macrophages," in *The Reticuloendothelial System*, S. M. Reichard and J. Filkins, Eds., Plenum, N.Y., pp. 315–327, 1985. As the diameter of particles exceeds 3 $\mu$m, there is increasingly less phagocytosis by macrophages. However, increasing the particle size also minimizes the probability of particles (possessing standard mass density) entering the airways and acini due to excessive deposition in the oropharyngeal or nasal regions. Heyder, J., et al., *J. AerosolAci.,* 17: 811–825 (1986). An effective slow-release inhalation therapy requires a means of avoiding or suspending the lung's natural clearance mechanisms until drugs have been effectively delivered.

Therapeutic dry-powder aerosols have been made as solid (macroscopically nonporous) particles, with mean diameters less than approximately 5 $\mu$m to avoid excessive oropharyngeal deposition. Ganderton, D., *J. Biopharmaceutical Sciences* 3: 101–105 (1992); and Gonda, I., "Physico-Chemical Principles in Aerosol Delivery," in *Topics in Pharmaceutical Sciences* 1991, Commelin, D. J. and K. K. Midha, Eds., Medpharm Scientific Publishers, Stuttgart, pp. 95–115, 1992.

There is a need for improved inhaled aerosols for pulmonary delivery of therapeutic agents. There is a need for the development of drug carriers which are capable of delivering the drug in an effective amount into the airways or the alveolar zone of the lung. There further is a need for the development of drug carriers for use as inhaled aerosols which are biodegradable and are capable of controlled release within the airways or in the alveolar zone of the lung.

It is therefore an object of the present invention to provide improved carriers for the pulmonary delivery of therapeutic agents. It is a further object of the invention to provide inhaled aerosols which are effective carriers for delivery of therapeutic agents to the deep lung. It is another object of the invention to provide carriers for pulmonary delivery which avoid phagocytosis in the deep lung. It is a further object of the invention to provide carriers for pulmonary drug delivery which are capable of biodegrading and releasing the drug at a controlled rate.

SUMMARY OF THE INVENTION

Improved porous particles for drug delivery to the pulmonary system, and methods for their synthesis and administration are provided. In a preferred embodiment, the porous particles are made of a biodegradable material and have a mass density less than 0.4 g/cm$^3$. The particles may be formed of biodegradable materials such as biodegradable polymers. For example, the particles may be formed of a functionalized polyester graft copolymer consisting of a linear α-hydroxy-acid polyester backbone having at least one amino acid group incorporated therein and at least one poly(amino acid) side chain extending from an amino acid group in the polyester backbone. In one embodiment, porous particles having a relatively large mean diameter, for example, greater than 5 μm, can be used for enhanced delivery of a therapeutic agent to the airways or the alveolar region of the lung. The porous particles incorporating a therapeutic agent may be effectively aerosolized for administration to the respiratory tract to permit systemic or local delivery of a wide variety of therapeutic agents.

DETAILED DESCRIPTION OF THE INVENTION

Figure 1:
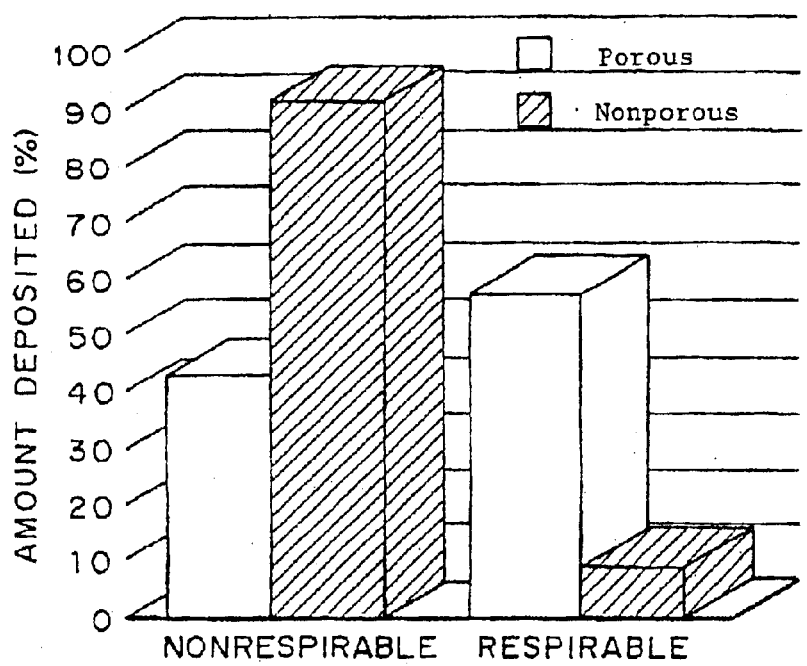
FIG. 1 is a graph comparing total particle mass of porous and non-porous particles deposited on the nonrespirable and respirable stages of a cascade impactor following aerosolization.

Biodegradable particles for improved delivery of therapeutic agents to the respiratory tract are provided. The particles can be used in one embodiment for controlled systemic or local drug delivery to the respiratory tract via aerosolization. In one embodiment, the particles are porous particles having a mass density less than 1.0 g/cm$^3$, preferably less than about 0.4 g/cm$^3$. The porous structure permits deep lung delivery of relatively large diameter therapeutic aerosols, for example greater than 5 μm in mean diameter. The particles also may include a rough surface texture which can reduce particle agglomeration and provide a highly flowable powder, which is ideal for aerosolization via dry powder inhaler devices, leading to lower deposition in the mouth and throat.

Mass Density and Diameter of Porous Particles

As used herein the term "porous particles" refers to particles having a total mass density less than about 0.4 g/cm$^3$. The mean diameter of the particles can range, for example, from about 100 nm to 15 μm, or larger depending on factors such as particle composition, and the targeted site of the respiratory tract for deposition of the particle.

Particle Size

In one embodiment, particles which are macroscopically porous, and incorporate a therapeutic drug, and having a mass density less than about 0.4 g/cm$^3$, can be made with mean diameters greater than 5 μm, such that they are capable of escaping inertial and gravitational deposition in the oropharyngeal region, and are targeted to the airways or the deep lung. The use of larger porous particles is advantageous since they are able to aerosolize more efficiently than smaller, non-porous aerosols such as those currently used for inhalation therapies.

The large (>5 μm) porous particles are also advantageous in that they can more successfully avoid phagocytic engulfment by alveolar macrophages and clearance from the lungs, in comparison to smaller non-porous particles, due to size exclusion of the particles from the phagocytes' cytosolic space. Phagocytosis of particles by alveolar macrophages diminishes precipitously as particle diameter increases beyond 3 μm. Kawaguchi, H. et al., *Biomaterials* 7: 61–66 (1986); Krenis, L. J. and Strauss, B., *Proc. Soc. Exp. Med.,* 107: 748–750 (1961); and Rudt, S. and Muller, R. H., *J. Contr. Rel.,* 22: 263–272 (1992). The porous particles thus are capable of a longer term release of a therapeutic agent. Following inhalation, porous degradable particles can deposit in the lungs (due to their relatively low mass density), and subsequently undergo slow degradation and drug release, without the majority of the particles being phagocytosed by alveolar macrophages. The drug can be delivered relatively slowly into the alveolar fluid, and at a controlled rate into the blood stream, minimizing possible toxic responses of exposed cells to an excessively high concentration of the drug. The porous polymeric particles thus are highly suitable for inhalation therapies, particularly in controlled release applications. The preferred diameter for porous particles for inhalation therapy is greater than 5 μm, for example between about 5–15 μm.

The particles also may be fashioned with the appropriate material, diameter and mass density for localized delivery to other regions of the repiratory tract such as the upper airways. For example higher density or larger particles may be used for upper airway delivery.

Particle Deposition

Inertial impaction and gravitational settling of aerosols are predominant deposition mechanisms in the airways and acini of the lungs during normal breathing conditions. Edwards, D. A., *J. Aerosol Sci.* 26: 293–317 (1995). Both deposition mechanisms increase in proportion to the mass of aerosols and not to particle volume. Since the site of aerosol deposition in the lungs is determined by the intrinsic mass of the aerosol (at least for particles of mean aerodynamic diameter greater than approximately 1 μm), diminishing particle mass density by increasing particle porosity permits the delivery of larger particles into the lungs, all other physical parameters being equal.

The low mass porous particles have a small aerodynamic diameter in comparison to the actual sphere diameter. The aerodynamic diameter, $d_{aer}$, is related to the actual sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers, 1992) by the formula:

$$d_{aer}=d\sqrt{\rho}$$

where the particle mass density ρ is in units of g/cm$^3$. Maximal deposition of monodisperse aerosol particles in the alveolar region of the human lung (~60%) occurs for an aerodynamic diameter of approximately $d_{aer}=3$ μm. Heyder, J. et al., *J. Aerosol Sci.,* 17: 811–825 (1986). Due to their small mass density, the actual diamter d of porous particles comprising a mondisperse inhaled powder that will exhibit maximum deep-lung deposition is:

$$d=3/\sqrt{\rho} \; \mu m \; (\text{where } \rho<1);$$

where d is always greater than 3 μm. For example, porous particles that display a mass density, ρ=0.1 g/cm$^3$, will exhibit a maximum deposition for particles having actual diameters as large as 9.5 μm. The increased particle size diminishes interparticle adhesion forces. Visser, J., *Powder Technology,* 58:1–10. Thus, large particle size increases efficiency of aerosolization to the deep lung for particles of low mass density.

Particle Materials

The porous particles preferably are biodegradable and biocompatible, and optionally are capable of biodegrading at a controlled rate for delivery of a drug. The porous particles can be made of any material which is capable of forming a porous particle having a mass density less than about 0.4 g/cm$^3$. Both inorganic and organic materials can be used. For example, ceramics may be used. Other non-polymeric materials may be used which are capable of forming porous particles as defined herein.

Polymeric Particles

The particles may be formed from any biocompatible, and preferably biodegradable polymer, copolymer, or blend, which is capable of forming porous particles having a density less than about 0.4 g/cm$^3$.

Surface eroding polymers such as polyanhydrides may be used to form the porous particles. For example, polyanhydrides such as poly[(p-carboxyphenoxy)hexane anhydride] ("PCPH") may be used. Biodegradable polyanhydrides are described, for example, in U.S. Pat. No. 4,857,311, the disclosure of which is incorporated herein by reference.

In another embodiment, bulk eroding polymers such as those based on polyesters including poly(hydroxy acids) can be used. For example, polyglycolic acid ("PGA") or polylactic acid ("PLA") or copolymers thereof may be used to form the porous particles, wherein the polyester has incorporated therein a charged or functionalizable group such as an amino acid as described below.

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses, polysaccharides, and peptides or proteins, or copolymers or blends thereof which are capable of forming porous particles with a mass density less than about 0.4 g/cm$^3$. Polymers may be selected with or modified to have the appropriate stability and degradation rates in vivo for different controlled drug delivery applications.

Polyester Graft Copolymers

In one preferred embodiment, the porous particles are formed from functionalized polyester graft copolymers, as described in Hrkach et al., *Macromolecules*, 28:4736–4739 (1995); and Hrkach et al., "Poly(L-Lactic acid-co-amino acid) Graft Copolymers: A Class of Functional Biodegradable Biomaterials" in *Hydrogel and Biodegradable Polymers for Bioapplications*, ACS Symposium Series No. 627, Raphael M. Ottenbrite et al, Eds., American Chemical Society, Chapter 8, pp. 93–101, 1996, the disclosures of which are incorporated herein by reference. The functionalized graft copolymers are copolymers of polyesters, such as poly(glycolic acid) or poly(lactic acid), and another polymer including functionalizable or ionizable groups, such as a poly(amino acid). In a preferred embodiment, comb-like graft copolymers are used which include a linear polyester backbone having amino acids incorporated therein, and poly(amino acid) side chains which extend from the amino acid groups in the polyester backbone. The polyesters may be polymers of a α-hydroxy acids such as lactic acid, glycolic acid, hydroxybutyric acid and valeric acid, or derivatives or combinations thereof. The inclusion of ionizable side chains, such as polylysine, in the polymer has been found to enable the formation of more highly porous particles, using techniques for making microparticles known in the art, such as solvent evaporation. Other ionizable groups, such as amino or carboxyl groups, may be incorporated, covalently or noncovalently, into the polymer to enhance porosity. For example, polyaniline could be incorporated into the polymer.

An exemplary polyester graft copolymer, which may be used to form porous polymeric particles is the graft copolymer, poly(lactic acid-co-lysine-graft-lysine) ("PLAL-Lys"), which has a polyester backbone consisting of poly (L-lactic acid-co-Z-L-lysine) (PLAL), and grafted lysine chains. PLAL-Lys is a comb-like graft copolymer having a backbone composition, for example, of 98 mol % lactic acid and 2 mol % lysine and poly(lysine) side chains extending from the lysine sites of the backbone.

PLAL-Lys may be synthesized as follows. First, the PLAL copolymer consisting of L-lactic acid units and approximately 1–2% Nε-carbobenzoxy-L-lysine (Z-L-lysine) units is synthesized as described in Barrera et al., *J. Am. Chem. Soc.*, 115:11010 (1993). Removal of the Z protecting groups of the randomly incorporated lysine groups in the polymer chain of PLAL yields the free e-amine which can undergo further chemical modification. The use of the poly(lactic acid) copolymer is advantageous since it biodegrades into lactic acid and lysine, which can be processed by the body. The existing backbone lysine groups are used as initiating sites for the growth of poly(amino acid) side chains.

The lysine ε-amine groups of linear poly(L-lactic acid-co-L-lysine) copolymers initiate the ring opening polymerization of an amino acid N-carboxyanhydride (NCA) to produce poly(L-lactic acid-co-amino acid) comb-like graft copolymers. In a preferred embodiment, NCAs are synthesized by reacting the appropriate amino acid with triphosgene. Daly et al., *Tetrahedron Lett.*, 29:5859 (1988). The advantage of using triphosgene over phosgene gas is that it is a solid material, and therefore, safer and easier to handle. It also is soluble in THF and hexane so any excess is efficiently separated from the NCAs.

The ring opening polymerization of amino acid N-carboxyanhydrides (NCAs) is initiated by nucleophilic initiators such as amines, alcohols, and water. The primary amino initiated ring opening polymerization of NCAs allows good control over the degree of polymerization when the monomer to initiator ratio (M/I) is less than 150. Kricheldorf, H. R. in *Models of Biopolymers by Ring-Opening Polymerization*, Penezek, S., Ed., CRC Press, Boca Raton, 1990, chapter 1; Kricheldorf, H. R., α-Aminoacid-N-Carboxy-Anhydrides and Related Heterocycles, Springer-Verlag, Berlin, 1987; and Imanishi, Y. in *Ring-Opening Polymerization*, Ivin, K. J. and Saegusa, T., Eds., Elsevier, London, 1984, Volume 2, chapter 8. Methods for using lysine ε-amine groups as polymeric initiators for NCA polymerizations are described in the art. Sela, M. et al., *J. Am. Chem. Soc.*, 78:746 (1956).

In the reaction of an amino acid NCA with PLAL, the nucleophilic primary ε-amine of the lysine side chain attacks C-5 of the NCA leading to ring opening and formation of the amino acid amide along with the evolution of $CO_2$. Propagation takes place via further attack of the amine group of the amino acid amides on subsequent NCA molecules. The degree of polymerization of the poly(amino acid) side chains, the corresponding amino acid content in the graft copolymers and their resulting physical and chemical characteristics can be controlled by changing the M/I ratio for the NCA polymerization—that is, changing the ratio of NCA to lysine ε-amine groups of pLAL. Thus, in the synthesis, the length of the poly(amino acid), such as poly(lysine), side chains and the total amino acid content in the polymer may be designed and synthesized for a particular application.

The poly(amino acid) side chains grafted onto or incorporated into the polyester backbone can include any amino acid, such as aspartic acid, alanine or lysine, or mixtures thereof. The functional groups present in the amino acid side chains, which can be chemically modified, include amino, carboxylic acid, sulfide, guanidino, imidazole and hydroxyl groups. As used herein, the term "amino acid" includes natural and synthetic amino acids and derivatives thereof. The polymers can be prepared with a range of amino acid side chain lengths, for example, about 10–100 or more amino acids, and with an overall amino acid content of, for example, 7–72% or more depending on the reaction conditions. The grafting of poly(amino acids) from the pLAL backbone may be conducted in a solvent such as dioxane, DMF, or $CH_2Cl_2$ or mixtures thereof. In a preferred embodiment, the reaction is conducted at room temperature for about 2–4 days in dioxane.

Alternatively, the porous particles for pulmonary drug delivery may be formed from polymers or blends of polymers with different polyester/amino acid backbones and grafted amino acid side chains. For example, poly(lactic acid-co-lysine-graft-alanine-lysine) ("PLAL-Ala-Lys"), or a blend of PLAL-Lys with poly(lactic acid-co-glycolic acid-block-ethylene oxide) ("PLGA-PEG") ("PLAL-Lys-PLGA-PEG") may be used.

In the synthesis, the graft copolymers may be tailored to optimize different characteristic of the porous particle including: i) interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity.

Formation of Porous Polymeric Particles

Porous polymeric particles may be prepared using single and double emulsion solvent evaporation, spray drying, solvent extraction and other methods well known to those of ordinary skill in the art. Methods developed for making microspheres for drug delivery are described in the literature, for example, as described by Mathiowitz and Langer, *J. Controlled Release Vol.* 5:13–22 (1987); Mathiowitz, et al., *Reactive Polymers*, 6:275–283 (1987); and Mathiowitz, et al., *J. Appl. Polymer Sci.* 35: 755–774 (1988), the teachings of which are incorporated herein. The selection of the method depends on the polymer selection, the size, external morphology, and crystallinity that is desired, as described, for example, by Mathiowitz, et al., *Scanning Microscopy* 4:329–340 (1990); Mathiowitz, et al., *J. Appl. Polymer Sci.* 45:125–134 (1992); and Benita, et al., *J. Pharm. Sci.* 73:1721–1724 (1984), the teachings of which are incorporated herein.

In solvent evaporation, described for example, in Mathiowitz, et al., (1990), Benita, and U.S. Pat. No. 4,272,398 to Jaffe, the polymer is dissolved in a volatile organic solvent, such as methylene chloride. Several different polymer concentrations can be used, for example, between 0.05 and 0.20 g/ml. The drug, either in soluble form or dispersed as fine particles, is added to the polymer solution, and the mixture is suspended in an aqueous phase that contains a surface active agent such as poly(vinyl alcohol). The aqueous phase may be, for example, a concentration of 1% poly (vinyl alcohol) w/v in distilled water. The resulting emulsion is stirred until most of the organic solvent evaporates, leaving solid microspheres, which may be washed with water and dried overnight in a lyophilizer.

Microspheres with different sizes (1–1000 microns) and morphologies can obtained by this method which is useful for relatively stable polymers such as polyesters and polystryrene. However, labile polymers such as polyanhydrides may degrade due to exposure to water. For these polymers, solvent removal may be preferred.

Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter for example between one and 300 microns can be obtained with this procedure.

Targeting of Particles

Targeting molecules can be attached to the porous particles via reactive functional groups on the particles. For example, targeting molecules can be attached to the amino acid groups of functionalized polyester graft copolymer particles, such as PLAL-Lys particles. Targeting molecules permit binding interaction of the particle with specific receptor sites, such as those within the lungs. The particles can be targeted by attachment of ligands which specifically or non-specifically bind to particular targets. Exemplary targeting molecules include antibodies and fragments thereof including the variable regions, lectins, and hormones or other organic molecules capable of specific binding for example to receptors on the surfaces of the target cells.

Therapeutic Agents

Any of a variety of therapeutic, prophylactic or diagnostic agents can be delivered. Examples include synthetic inorganic and organic compounds, proteins and peptides, polysaccharides and other sugars, lipids, and nucleic acid sequences having therapeutic, prophylactic or diagnostic activities. Nucleic acid sequences include genes, antisense molecules which bind to complementary DNA to inhibit transcription, and ribozymes. The agents to be incorporated can have a variety of biological activities, such as vasoactive agents, neuroactive agents, hormones, anticoaguulants, immunomodulating agents, cytotoxic agents, antibiotics, antivirals, antisense, antigens, and antibodies. In some instances, the proteins may be antibodies or antigens which otherwise would have to be administered by injection to elicit an appropriate response. Compounds with a wide range of molecular weight can be encapsulated, for example, between 100 and 500,000 grams per mole.

Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered.

The porous polymeric aerosols are useful as carriers for a variety of inhalation therapies. They can be used to encapsulate small and large drugs, release encapsulated drugs over time periods ranging from hours to months, and withstand extreme conditions during aerosolization or following deposition in the lungs that might otherwise harm the encapsulated therapeutic.

The porous particles may include a therapeutic agent for local delivery within the lung, such as agents for the treatment of asthma, emphysema, or cystic fibrosis, or for systemic treatment. For example, genes for the treatment of diseases such as cystic fibrosis can be administered.

Administration

The particles including a therapeutic agent may be administered alone or in any appropriate pharmaceutical carrier, such as a liquid, for example saline, or a powder, for administration to the respiratory system.

Aerosol dosage, formulations and delivery systems may be selected for a particular therapeutic application, as described, for example in Gonda, I. "Aerosols for delivery of therapeutic and diagnostic agents to the respiratory tract," in *Critical Reviews in Therapeutic Drug Carrier Systems*, 6:273–313 (1990), and in Moren, "Aerosol dosage forms and formulations," in *Aerosols in Medicine. Principles, Diagnosis and Therapy*, Moren, et al., Eds., Esevier, Amsterdam, 1985, the disclosures of which are incorporated herein by reference.

The greater efficiency of aerosolization by porous particles of relatively large size permits more drug to be delivered than is possible with the same mass of nonporous aerosols. The relative large size of porous aerosols depositing in the deep lungs also minimizes potential drug losses caused by particle phagocytosis. The use of porous polymeric aerosols as therapeutic carriers provides the benefits of biodegradable polymers for controlled released in the lungs and long-time local action or systemic bioavailability. Denaturation of macromolecular drugs can be minimized during aerosolization since macromolecules are contained and protected within a polymeric shell. Coencapsulation of peptides with peptidase-inhibitors can minimize peptide enzymatic degradation.

The present invention will be further understood by reference to the following non-limiting examples.

Example 1

Synthesis of Porous Poly[(p-carboxyphenoxy)-hexane anhydride] ("PCPH") Particles Porous poly[(p-carboxyphenoxy)-hexane anhydride] ("PCPH") particles were synthesized as follows. 100 mg PCPH (MW-25,000) was dissolved in 3.0 mL methylene chloride. To this clear solution was added 5.0 mL 1% w/v aqueous polyvinyl alcohol (PVA, MW ~25,000, 88 mole % hydrolyzed) saturated with methylene chloride, and the mixture was vortexed (Vortex Genie 2, Fisher Scientific) at maximum speed for one minute. The resulting milky-white emulsion was poured into a beaker containing 95 mL 1% PVA and homogenized (Silverson Homogenizers) at 6000 RPM for one minute using a 0.75 inch tip. After homogenization, the mixture was stirred with a magnetic stirring bar and the methylene chloride quickly extracted from the polymer particles by adding 2 mL isopropyl alcohol. The mixture was continued to stir for 35 minutes to allow complete hardening of the microparticles. The hardened particles were collected by centrifugation and washed several times with double distilled water. The particles were freeze dried to obtain a free-flowing powder void of clumps. Yield, 85–90%.

The mean diameter of this batch was 6.0 $\mu$m, however, particles with mean diameters ranging from a few hundred nanometers to several millimeters may be made with only slight modifications. Scanning electron micrograph photos of a typical barch of PCPH particles showed the particles to be highly porous. The particles have a mass density less that 1 g/cm$^3$ as indicated by the fact that the particles float when dispersed in an organic solvent.

Example 2

Synthesis of PLAL-Lys and PLAL-Lys-Ala Polymeric and Copolymeric Particles

Porous PLAL-Lys Particles

PLAL-Lya particles were prepared by dissolving 50 mg of the graft copolymer in 0.5 ml dimethylsulfoxide, then adding 1.5 ml dichloromethane dropwise. The polymer solution is emulsified in 100 ml of 5% w/v polyvinyl alcohol solution (average molecular weight 25 KDa, 88% hydrolyzed) using a homogenizer (Silverson) at a speed of approximately 7500 rpm. The resulting dispersion is stirred using a magnetic stirrer for 1 hour. Following this period, the pH is brought to 7.0–7.2 by addition of 0.1 N NaOH solution. Stirring is continued for an additional 2 hours until the methylene chloride is completely evaporated and the particles hardened. The particles are then isolated by centrifugation at 4000 rpm (1600 g) for 10 minutes (Sorvall RX-5B). The supernatant is discarded and the precipitate washed three times with distilled water, the dispersion frozen in liquid nitrogen, and lyophilized (Labconco freeze dryer 8) for at least 48 hours. Particle sizing is performed using a Coulter counter. Average particle mean diameters ranged from 100 nm to 14 $\mu$m, depending upon processing parameters such as homogenization speed and time. All particles exhibit high porosity (net mass density less than 0.4 g/cm$^3$). Scanning electron micrograph photos of the particles showed them to be highly porous.

Porous PLAL-Ala-Lys Particles 100 mg of PLAL-Ala-Lys is completely dissolved in 0.4 ml trifluoroethanol, then 1.0 ml methylene chloride is added dropwise. The polymer solution is emulsified in 100 ml of 1% w/v polyvinyl alcohol solution (average molecular weight 25 KDa, 80% hydrolyzed) using a sonicator (Sonic&Materal VC-250) for 15 seconds at an output of 40 W. 2 ml of 1% PVA solution is added to the mixture and it is vortexed at the highest speed for 30 seconds. The mixture is quickly poured into a beaker containing 100 ml 0.3% PVA solution, and stirred for three hours allowing evaporation of the methylene chloride. Scanning electron micrograph photos of the particles showed them to be highly porous.

Porous Copolymer Particles

Polymeric porous particles consisting of a blend of PLAL-Lys ad PLGA-PEG were made. 50 mg of the PLGA-PEG polymer (molecular weight of PEG: 20 KDa, 1:2 weight ratio of PEG:PLGA, 75:25 lactide:glycolide) was completely dissolved in 1 ml dichloromethane. 3 mg of poly(lactide-co-lysine)-polylysine graft copolymer is dissolved in 0.1 ml dimethylsulfoxide and mixed with the first polymer solution. 0.2 ml TE buffer, pH 7.6, is emulsified in the polymer solution by probe sonication (Sonic&Materal VC-250) for 10 seconds at an output of 40W. To this first emulsion, 2 ml of distilled water is added and mixed using a vortex mixer at 4000 rpm for 60 seconds. The resulting dispersion is agitated by using a magnetic stirrer for 3 hours until methylene chloride is completely evaporated and microspheres formed. The spheres are then isolated by centrifugation at 5000 rpm for 30 min. The supernatant is discarded, the precipitate washed three times with distilled water and resuspended in 5 ml of water. The dispersion is frozen in liquid nitrogen and lyophilized for 48 hours.

Variables which may be manipulated to alter the size distribution of the particles include: polymer concentration, polymer molecular weight, surfactant type (e.g., PVA, PEG, etc.), surfactant concentration, and mixing intensity. Variables which may be manipulated to alter the porosity of the particles include: polymer concentration, polymer molecular weight, rate of methylene chloride extraction by isopropyl alcohol (or another miscible solvent), volume of isopropyl alcohol added, inclusion of an inner water phase, volume of inner water phase, inclusion of salts or other highly water-soluble molecules in the inner water phase which leak out of the hardening sphere by osmotic pressure, causing the formation of channels, or pores, in proportion to their concentration, and surfactant type and concentration.

By scanning electron microscopy (SEM), the PLAL-Lys-PLGA-PEG particles were highly porous. The particles had a mean particle diameter of 7 $\mu m \pm 3.8$ $\mu m$. The blend of PLAL-Lys with poly(lactic acid) (PLA) and/or PLGA-PEG copolymers can be adjusted to adjust particle porosity and size. Additionally, processing parameters such as homogenization speed and time can be adjusted. Neither PLAL, PLA nor PLGA-PEG alone yields a porous structure when prepared by these techniques.

Example 3

Rhodamine Isothiocyanate Labeling of PLAL and PLAL-Lys Particles

Lysine amine groups on the surface or porous (PLAL-Lys) and nonporous (PLAL) microparticles with similar mean diameters (6–7 $\mu m$) and size distributions (standard deviations 3–4 $\mu m$) were labeled with Rhodamine isothiocyanate. The mass density of the porous PLAL-Lys particles was 0.1 g/cm$^3$ and that of the nonporous PLAL particles was 0.8 g/cm$^3$.

The rhodamine-labeled particles were characterized by confocal microscopy. A limited number of lysine functionalities on the surface of the solid particle were able to react with rhodamine isothiocyanate, as evidenced by the flourescent image. In the porous particle, the higher lysine content in the graft copolymer and the porous particle structure result in a higher level of rhodamine attachment, with rhodamine attachment dispersed throughout the interstices of the porous structure. This also demonstrates that targeting molecules can be attached to the porous particles for interaction with specific receptor sites within the lungs via chemical attachment of appropriate targeting agents to the particle surface.

Example 4

Aerosolization of PLAL and PLAL-Lys Particles

To determine whether large porous particles can escape (mouth, throat, and inhaler) deposition and more efficiently enter the airways and acini than nonporous particles of similar size, aerosolization and deposition of porous PLAL-Lys (mean diameter 6.3 $\mu m \pm 3.3$ $\mu m$) or nonporous PLAL (mean diameter 6.9 $\mu m \pm 3.6$ $\mu m$) particles were examined in vitro using a cascade impactor system.

20 mg of the porous or nonporous microparticles were placed in gelatin capsules (Eli Lilly), the capsules loaded into a Spinhaler dry powder inhaler (DPI) (Fisons), and the DPI activated. Particles were aerosolized into a Mark I Andersen Impactor (Anderson Samplers, Ga.) from the DPI for 30 seconds at 28.3 l/min flow rate. Each plate of the Andersen Impactor was previously coated with Tween 80 by immersing the plates in an acetone solution (5% w/vol) and subsequently evaporating the acetone in a oven at 60° for 5 min. After aerosolization and deposition, particles were collected from each stage of the impactor system in separate volumetric flasks by rinsing each stage with NaOH solution (0.2 N) in order to completely degrade the polymers. After incubation at 37° C. for 12 h, the fluorescence of each solution was measured (wavelengths of 554 nm excitation, 574 nm emission).

Particles were determines as nonrespirable (mean aerodynamic diameter exceeding 4.7 $\mu m$: impactor estimate) if they deposited on the first three stages of the impactor, and respirable (mean aerodynamic diameter 4.7 $\mu m$ or less) if they deposited on subsequent stages. FIG. 1 shows that less than 10% of the nonporous (PLAL) particles that exit the DPI are respirable. This is consistent with the large size of the microparticles and their standard mass density. On the other hand, greater the 55% of the porous (PLAL-Lys) particles are respirable, even though the geometrical dimensions of the two particle types are almost identical. The lower mass density of the porous (PLAL-Lys) microparticles is responsible for this improvement in particle penetration, as discussed further below.

The nonporous (PLAL) particles also inefficiently aerosolize from the DPI; typically, less than 40% of the nonporous particles exited the Spinhaler DPI for the protocol used. The porous (PLAL-Lys) particles exhibited much more efficient aerosolization (approximately 80% if the porous microparticles typically exited the DPI during aerosolization).

The combined effects of efficient aerosolization and high respirable fraction of aerosolized particle mass means that a far greater fraction of a porous particle powder is likely to deposit in the lungs than of a nonporous particle powder.

Example 5

In Vivo Aerosolization of PLAL and PLAL-Lys Particles

The penetration of porous and non-porous polymeric PLAL and PLAL-Lys microparticles into the lungs was evaluated in and in vivo experiment involving the aerosolization of the microparticles into the airways of live rats.

Male Sprague Dawley rats (150–200 g) were anesthetized using ketamine (90 mg/kg)/xylazine (10 mg/kg). The anesthetized rat was placed ventral side up on a surgical table provided with a temperature controlled pad to maintain physiological temperature. The animal was cannulated about the carina with an endotracheal tube connected to a Harvard ventilator. The animal was force ventilated for 20 minutes and 300 ml/min. 50 mg of porous (PLAL-Lys) or nonporous (PLA) microparticles were introduced into the endotracheal tube.

Following the period of forced ventilation, the animal was euthanized and the lungs and trachea were separately washed using bronchoalveolar lavage. A tracheal cannula was inserted, tied into place, and the airways were washed with 10 ml aliquots of HBSS. The lavage procedure was repeated until a total volume of 30 ml was collected. The lavage fluid was centrifuged (400 g) and the pellets collected and resuspended in 2 ml of phenol red-free Hanks balanced salt solution (Gibco, Grand Island, N.Y.) without $Ca^{2+}$ and $Mg^{2+}$ (HBSS). 100 ml were removed for particle counting using a hemacytometer. The remaining solution was mixed with 10 ml of 0.4 N NaOH. After incubation at 37° C. for 12 h, the fluorescence of each solution was measured (wavelengths of 554 nm excitation, 574 nm emission).

Figure 2:
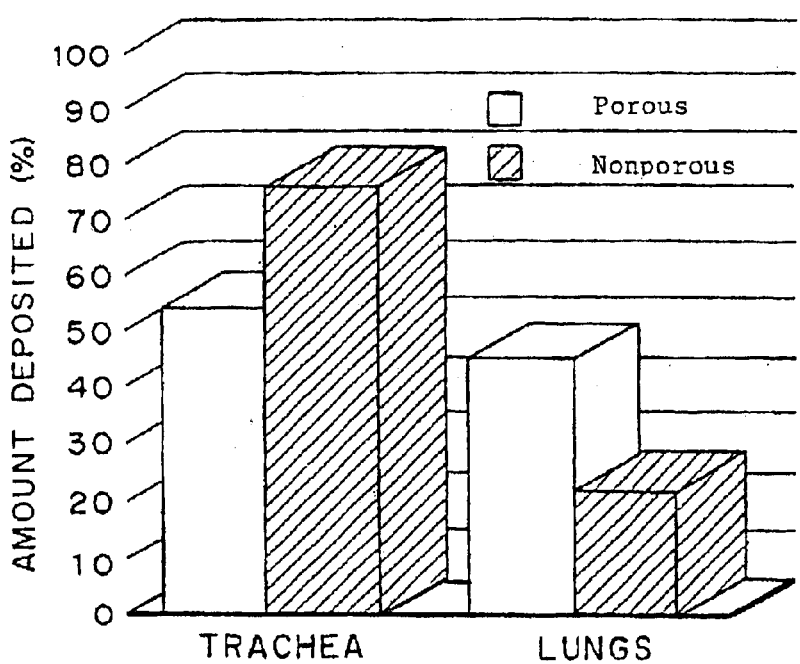
FIG. 2 is a graph comparing total particle mass deposited in the trachea and after the carina (lungs) in rat lungs and upper airways following intratracheal aerosolization during forced ventilation of porous PLAL-Lys particles and non-porous PLAL particles.
Figure 3:
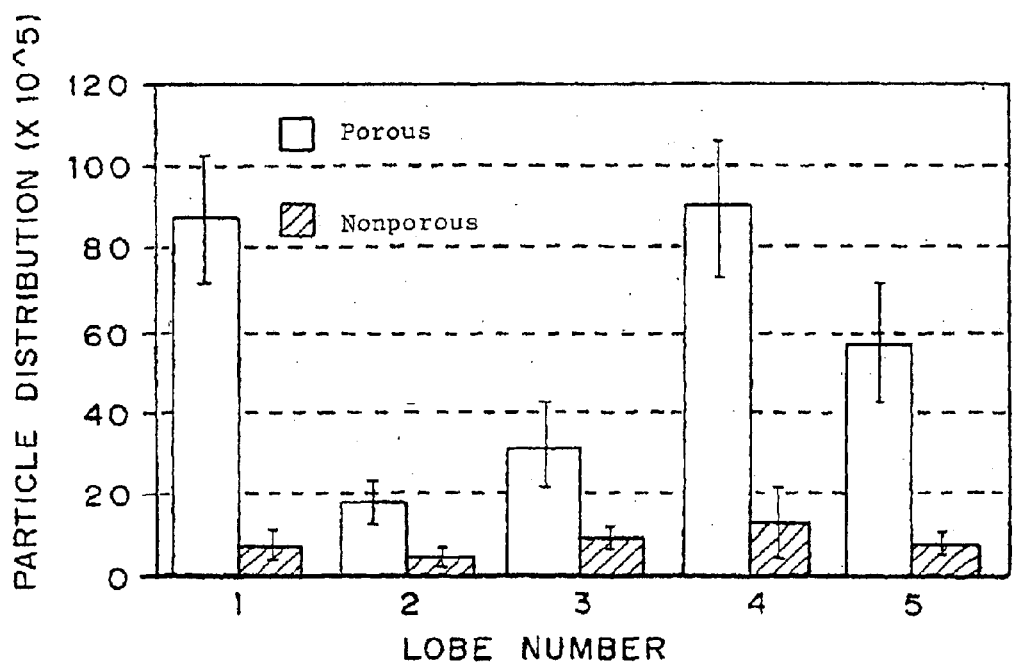
FIG. 3 is a graph comparing total particle recovery of porous PLAL-Lys particles and non-porous PLAL particles in rat lungs and following broncho alveolar lavage.

FIG. 2 is a bar graph showing total particle mass deposited in the trachea and after the carina (lungs) in rat lungs and upper airways following intratracheal aerosolization during forced ventilation. The PLAL-Lys porous particles had a mean diameter 6.9 μm±4.2 μm. The nonporous particles PLAL particles had a mean diameter of 6.7 μm±3.2 μm. Percent tracheal porous particle deposition was 54.54±0.77, and nonporous deposition was 76.98±1.95. Percent porous particle deposition in the lungs was 46.75±0.77, and nonporous deposition was 23.02±1.95.

The nonporous (PLAL) particles deposited primarily in the trachea (approximately 79% of all particle mass that entered the trachea). This result is similar to the in vitro performance of the nonporous microparticles and is consistent with the relatively large size of the nonporous particles. Approximately 54% if the porous (PLAL-Lys) particle mass deposited in the trachea. Therefore, about half of the porous particle mass that enters the trachea traverses through the trachea and into the airways and acini of the rat lungs, demonstrating the effective penetration of the porous particles into the lungs.

Following bronchoalveolar lavage, particles remaining in the rat lungs were obtained by careful dissection of the individual lobes of the lungs. The lobes were placed in separate petri dishes containing 5 ml of HBSS. Each lobe was teased through 60 mesh screen to dissociate the tissue and was then filtered through cotton gauze to remove tissue debris and connective tissue. The petri dish and gauze were washed with an additional 15 ml of HBSS to maximize microparticle collection. Each tissue preparation was centrifuged and resuspended in 2 ml of HBSS and the number of particles counted in a hemacytometer. The particle numbers remaining in the lungs following the bronchoalveolar lavage are shown in FIG. 3. Lobe numbers correspond to: 1) left lung, 2) anterior, 3) median, 4) posterior, 5) postcaval. A considerably greater number of porous PLAL-Lys particles enters every lobe of the lungs than the nonporous PLAL particles, even though the geometrical dimensions of the two types of particles are essentially the same. These results reflect both the efficiency of porous particle aerosolization and the propensity of the porous particles to escape deposition prior to the carina or first bifurcation.

Modifications and variations of the present invention will be obvious to those skilled in the art from the foregoing detailed description. Such modifications and variations are intended to come within the scope of the following claims.

What is claimed is:

1. An essentially dry composition comprising:

spray dried particles for delivering a therapeutic agent to the deep lung, wherein the particles comprise a therapeutic agent and at least 55% of the particles have an aerodynamic diameter less than about 4.7 μm as measured by a Mark I Anderson Impactor for 30 seconds at 28.3 l/min flow rate wherein the particles have a mass density less than about 0.1 g/$cm^3$.

2. The composition of claim 1, wherein the particles have a mass mean diameter between 5 μm and 30 μm.

3. The composition of claim 1, wherein the particles further comprise a pharmaceutically acceptable excipient.

4. The composition of claim 3, wherein the pharmaceutically acceptable excipient is selected from the group consisting of organic compounds, inorganic compounds, surfactants and any combinations thereof.

5. The composition of claim 4, wherein the pharmaceutically acceptable excipient is a surfactant.

6. The composition of claim 1, wherein the agent is selected from the group consisting of proteins, peptides, polysaccharides, lipids, nucleic acids and combinations thereof.

7. The composition of claim 1, wherein the agent is selected from the group consisting of antibodies, antigens, antibiotics, antivirals, hormones, vasoactive agents, neuroactive agents, anticoagulants, immunomodulating agents, cytotoxic agents, ribozymes, antisense agents and genes.

8. The composition of claim 1, for use in local inhalation therapy.

9. The composition of claim 8, wherein the agent is an agent for the treatment of asthma, emphysema, or cystic fibrosis.

10. The composition of claim 1, for use in systemic inhalation therapy.

11. The composition of claim 10, wherein the agent is insulin.

12. A method of delivering an essentially dry composition to the deep lung of the pulmonary system comprising: administering to the respiratory tract an effective amount of an essentially dry composition comprising spray dried particles for delivering a therapeutic agent;

wherein the particles comprise a therapeutic agent and at least 55% of the particles have an aerodynamic diameter less than about 4.7 μm as measured by a Mark I Anderson Impactor for 30 seconds at 28.3 l/min flow rate wherein the particles have a mass density less than about 0.1 g/$cm^3$.

13. The method of claim 12, wherein the particles have a mass mean diameter between 5 μm and 30 μm.

14. The method of claim 12, wherein the particles further comprise a pharmaceutically acceptable excipient.

15. The method of claim 14, wherein the pharmaceutically acceptable excipient is selected from the group consisting of organic compounds, inorganic compounds, surfactants and any combinations thereof.

16. The method of claim 15, wherein the pharmaceutically acceptable excipient is a surfactant.

17. The method of claim 12, wherein the agent is selected from the group consisting of proteins, peptides, polysaccharides, lipids, nucleic acids and combinations thereof.

18. The method of claim 12, wherein the agent is selected from the group consisting of antibodies, antigens, antibiotics, antivirals, hormones, vasoactive agents, neuroactive agents, anticoagulants, immunomodulating agents, cytotoxic agents, ribozymes, antisense agents and genes.

19. The method of claim 12, for use in local inhalation therapy.

20. The method of claim 19, wherein the agent is an agent for the treatment of asthma, emphysema, or cystic fibrosis.

21. The method of claim 12, for use in systemic inhalation therapy.

22. The method of claim 21, wherein the agent is insulin.

23. The method of claim 12, therein delivery is by dry powder inhaler.

* * * * *